April 20, 1965 O. O. DUNHAM Plant Pat. 2,498
CHRYSANTHEMUM PLANT
Filed Feb. 24, 1964
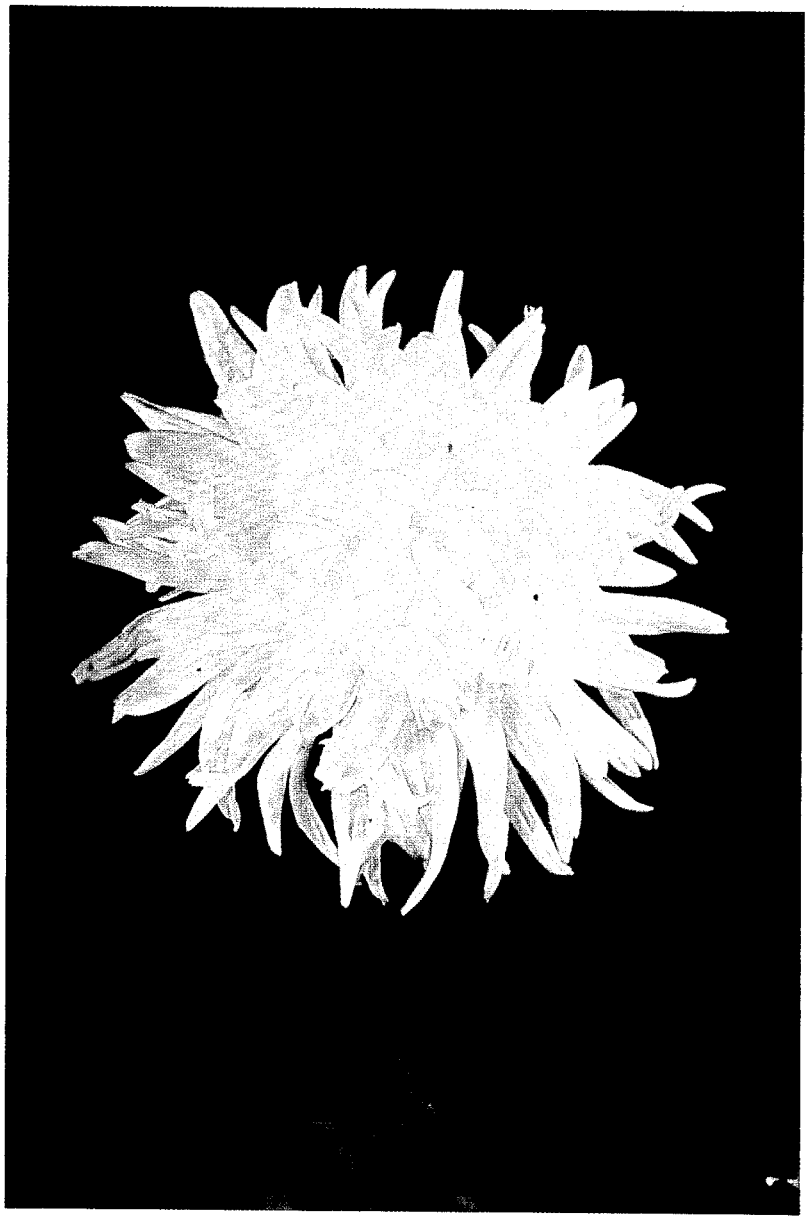
Inventor
O. O. Dunham
by Robb & Robb
attorneys United States Patent Office Plant Pat. 2,498
Patented Apr. 20, 1965

2,498
CHRYSANTHEMUM PLANT

Orville O. Dunham, Niles, Mich., assignor to Stern's Nurseries, Inc., Geneva, N.Y., a corporation of New York Filed Feb. 24, 1964, Ser. No. 347,103
1 Claim. (Cl. Plt.—78)

My present invention comprises a new and distinct variety of chrysanthemum plant resulting from the crossing of the variety disclosed in Plant Patent No. 2,006, with a variety of my own origination, which I designate "Adventure" and which is unpatented.

During the course of many years of hybridization, and particularly in the chrysanthemum art, I have developed from time to time a number of different varieties of chrysanthemum plant which partake of the desirable characteristics of both parents, in this instance the seed parent Plant Patent No. 2,006 contributing the earliness to bloom, and the solid, compact form of bloom being derived from the pollen parent "Adventure" (unpatented).

As a result of the planned hybridization herein referred to, in this particular plant, the seed parent likewise appears to have supplied the brilliant yellow color and fluffy petals of the blooms, the large size of the blooms originating from the pollen parent "Adventure."

The new variety is superior in many respects to either parent, since it combines certain desirable features of each as will be further set forth hereinafter.

The result of the hybridization previously referred to has been to produce my present new and distinct variety of chrysanthemum plant characterized by the brilliant yellow color of its blooms, the very large, tight incurved form of the blooms, notched, fluffy petals, the long, strong, stems with very large leaves of moderate olive green color, and early, continuous blooming period.

More specifically, the blooms of my new variety of chrysanthemum plant are of a brilliant yellow general tonality (Nickerson Color Fan published by the Munsell Color Company), with the bases of certain of the petals presenting a greenish-yellow and modifying the appearance of the bloom in some aspects. As grown in the vicinity of Niles, Michigan, in uniform culture, plants of my new variety grow to a height of 24 inches.

A notable feature of the blooms of my new variety is their very large size, many of them being from 6 to 7 inches in diameter and appearing from early in September until the end of the season.

Under the conditions of culture previously mentioned, which were undertaken in the region of Niles, Michigan, plants of my new variety grow vigorously with profuse production of blooms continuously as before stated until the killing frost in late fall.

My new variety has been asexually reproduced by cuttings in the vicinity of Niles, Michigan, observations made herein as a basis taking place during mid-October.

My new variety has been found to retain its distinctive characteristics through successive asexual reproduction.

The accompanying drawing forming a part hereof shows a typical bloom of my new variety of chrysanthemum in a color illustration which is substantially accurate as is possible in color illustrations of this nature.

The following is a detailed description of my new variety of chrysanthemum plant, the color references being to the Nickerson Color Fan published by the Munsell Color Company:

*Description*

Parentage: Seedling.
*Seed parent.*—Plant Patent No. 2,006.
*Pollen parent.*—"Adventure" (unpatented).
Classification: Botanic—*Chrysanthemum indicum.*

*Flower*

Blooming habit: Blooms from early September, profusely and continuously to a killing frost in late fall.
Bud:
*Size.*—Large.
*Form.*—Short with flat top.
Not affected noticeably by wet or hot weather.
Color:
*When sepals first divide.*—7.5Y 9/8.
*When petals begin to unfurl.*—5Y 8/12.
*When half blown.*—Inside of petals—5Y 9/9. Reverse of petals—5Y 9/9.
*Calyx.*—Shape—funnel. Size—large and broad. Aspect—hairy.
*Peduncle.* — Length. — medium. Aspect — rough. Strength—stiff and erect. Bud opens well.
Bloom:
*Size.*—Very large.
*Average size when fully expanded.*—6 to 7 inches.
*Borne.*—In clusters and rounded.
*Stems.*—Long and strong.
*Form.* — When first open — cupped. Permanence—retains its form to the end.
*Petalage.*—Very double; innumerable petals under normal conditions.
Color:
*Center of flower.*—5Y 9/9 Brilliant Yellow.
*Outer petals.*—5Y 9/9 Brilliant yellow.
*Base of petals (singlet).*—10Y 9/9 Brilliant Greenish-Yellow.
*Inside of petals.*—5Y 9/9 Brilliant Yellow.
*Reverse of petals.*—5Y 9/9 Brilliant Yellow.
*General tonality from a distance.*—Brilliant yellow.
*Discoloration.*—General tonality at end of: First week—brilliant yellow. Second and third week—retains same color.
Petals:
*Texture.*—Thick and soft. Is not affected by hot or wet weather.
*Appearance.*—Inside—velvety. Outside—satiny.
*Form.*—Notched.
*Arrangement.*—Irregular.
*Persistence.*—Hang on and dry.
*Fragrance.*—None.
*Lastingness.*—On the plant—very long. As a cut flower—very long.
Genital organs:
*Stamens, anthers.*—Medium, few.
*Arrangement.*—Regular around styles.
*Stamens, filaments.*—Medium.
*Styles.*—Columnar.
Plant:
*Form.*—Bush.
*Growth.*—Vigorous, upright and branching.
Foliage:
*Size.*—Very large.
*Quantity.*—Abundant.
*Color (new foliage).*—Upper side—7.5GY 4/4 Moderate Olive Green. Under side—7.5GY 5/7 Moderate Yellow-Green.

*Texture.* — Upper side — glossy. Under side— velvety.
*Ribs and veins.*—Ordinary.
*Edge.*—Serrated.
*Serration.*—Single.

I claim:

A new and distinct variety of chrysanthemum plant substantially as herein disclosed, characterized as to novelty by the brilliant yellow color of its blooms, the very large, tight incurved form of the blooms, notched, fluffy petals, long, strong, stems with very large leaves of moderate olive green color, and early, continuous blooming period.

No references cited.

ABRAHAM G. STONE, *Primary Examiner.*